United States Patent [19]

Trexler

[11] 4,366,809
[45] Jan. 4, 1983

[54] ISOLATION ENCLOSURE MEMBERS

[76] Inventor: Philip C. Trexler, 2 Brook Cottage, Bagshot, Surrey, England

[21] Appl. No.: 309,844

[22] Filed: Oct. 8, 1981

Related U.S. Application Data

[63] Continuation of Ser. No. 56,690, Jul. 11, 1979, abandoned.

[30] Foreign Application Priority Data

Jul. 17, 1978 [GB] United Kingdom ............... 30077/78

[51] Int. Cl.³ ............................................ A61M 16/02
[52] U.S. Cl. .............................. 128/1 R; 128/205.26; 128/202.12; 312/1; 312/3; 312/6; 52/2
[58] Field of Search ................... 128/1 R, 1 B, 205.26, 128/297, 298, 202.12; 312/1, 3, 6; 52/2

[56] References Cited

U.S. PATENT DOCUMENTS 3,450,450 6/1969 Hopkins et al. ......................... 312/1
4,026,286 5/1977 Trexler ................................. 128/1 B

FOREIGN PATENT DOCUMENTS

3004066 8/1981 Fed. Rep. of Germany .......... 312/1
1436104 5/1976 United Kingdom ................ 128/1 B Primary Examiner—Henry J. Recla
Attorney, Agent, or Firm—Cushman, Darby & Cushman

[57] ABSTRACT

An exclusion or containment isolator provides an isolated environment for example for surgery or for preventing spread of infection. Known sleeves for allowing operators to manipulate inside the isolator from outside present difficulties in manufacture and can reduce easy movement of the operators arms. An isolator (11) of flexible, transparent plastics material has wide, triangular sleeves (35, 36) extending from regions of conjunction (44, 45) with the main isolator body (43), the regions of conjunction partially overlying one another to give greater freedom of movement. Preferably the sleeve construction utilizes a side sheet (13) providing a lower wall (25) of one sleeve (35) and upper wall (27) of the next adjacent sleeve (36).

17 Claims, 8 Drawing Figures

ISOLATION ENCLOSURE MEMBERS

This is a continuation of application Ser. No. 56,690 filed July 11, 1979 and now abandoned.

The present invention relates to enclosure members for providing an environment isloated from the ambient environment, and to methods of making such enclosure members. The invention is concerned in particular, although not exclusively, with such enclosure members adapted for use in the performance of surgical operations.

The invention is concerned with enclosure members which have become known as isolators and which have as their purpose the provision of an environment isolated from the ambient environment. One use of an isolator is for the handling of laboratory animals and human patients under controlled microbiological conditions in which only known microbes are present in the environment of the subject, and these conditions have been known as gnotobiotic conditions. Such an isolator is known as an exclusion isolator and is usually maintained at a small positive air pressure with respect to the ambient atmosphere. Another use of an isolator is for the containment of infection where a patient is suffering from an infectious disease. In such use it is arranged to operate the isolator at a pressure slightly below ambient pressure, and such isolators are known as containment isolators.

Another example of medical use of an isolator is the use of an exclusion isolator in the preparation or packaging of drugs for medical purposes. Other uses arise in industrial circumstances in the manufacture of components requiring great cleanliness, where dust and other contaminants need to be excluded. A further example of a use of a containment isolator arises in the handling of radioactive or other contaminated materials.

An isolator commonly consists of a flexible bag of transparent plastics material forming an enclosure which is continuously vented with germ-free air. Sometimes the isolators are in disposable form, being provided pre-sterilized for use on one occasion only.

In the exclusion mode it is usual for the air pressure in the enclosure at least to contribute to the maintenance of the isolator in an erected condition. In the containment mode, the isolation enclosure member is commonly suspended from a surrounding framework. The boundary wall of an exclusion or containment isolator may be formed wholly or only partly by flexible synthetic plastics material.

Isolators will normally have means for handling objects within the enclosure without breaking the microbiological or other isolation of the enclosure, and commonly these handling means will comprise flexible sleeves set into a wall of the isolator enclosure member into which an operator's arms can be inserted. The sleeves are commonly provided with wrist-length gloves which are sealed at the ends of the sleeves.

The normal method of producing such sleeves is to provide a conical sleeve which is secured to a main body of the isolator enclosure member by being welded to a circular opening in the main body with a weld around a circular join line. Such a method of manufacture is time consuming, requires skill on the part of the operator making the isolator, and requires relatively expensive equipment capable of providing a weld around a curved line. There are a number of advantages in manufacturing isolators by techniques avoiding the need to weld around complete circles to attach sleeves. Attempts have been made to make small isolators by welding together along substantially straight lines flat upper and lower sheets with sleeves formed by protruding elongated portions at the edges of the sheets. The disadvantage has been found that although the sleeves are of conventional shape when formed in the flat condition, when the sleeves are 'rounded out' during use with the operator's arms in the sleeves, there is insufficient material available around the shoulder portions to allow the required freedom of movement for the operator. This is particularly acute where the isolator is used for surgical purposes since a number of operators are required to be positioned relatively close together along the side of the isolator. The isolator sleeves are normally positioned in pairs side by side along the side of the isolator and in such conditions the limiting factors on the freedom of movement of the operators are the width of the shoulders of the normal human operator, and the close positioning of adjacent operators during a surgical operation. Where attempts have been made to produce surgical isolators with flat, straight-welded, sleeves these difficulties are compounded by the puckering and wrinkling effect when the flat, straight-welded sleeve is 'rounded out' by insertion of the operator's arm.

The present invention seeks to provide, in some aspects, isolators which at least reduce the limitations on the freedom of movement of an operator using sleeves in the side of an isolator, and in other aspects to provide a method of making enclosure members which method avoids the need for attaching sleeves with welds around complete circles and in which method the previous disadvantages of insufficient freedom of movement for the operator are at least reduced. In some aspects of the invention, both these improvements may be obtained.

According to the present invention there is provided an enclosure member for providing an environment isolated from the ambient environment, the enclosure member having first and second flexible sleeves extending from a side of a main body of the enclosure member, the first sleeve extending from a first region of conjunction with the main body of the enclosure member, and the second sleeve extending from a second region of conjunction with the main body of the enclosure member, the general longitudinal axes of the sleeves being spaced apart along the side of the enclosure member for the sleeves to accommodate the arms of an operator manipulating objects inside the enclosure member during normal use of the enclosure member, wherein the said first region of conjunction partially overlies the said second region of conjunction when viewed vertically from above when the enclosure member is in normal use.

It is to be appreciated that the said regions of conjunction are not necessarily defined by a join in the materials of the main body of the enclosure member and the sleeves. Such a join in the materials of a sleeve and the main body of the enclosure member may be present in some arrangements, but in preferred arrangements according to the invention at least part of a sleeve will be formed by a sleeve panel which is continuous with a wall of the main body of the enclosure member.

The said regions of conjunction may consist of discrete separate regions of conjunction of the sleeves with the main body of the enclosure member, or the regions of conjunction may merge or may extend in part over a common area.

Preferably the first region of conjunction overlies the second region of conjunction to the extent of a proportion of the width of the second region of conjunction taken along the side of the enclosure member, the said proportion lying in the range 0.25 to 0.75 of the width of the second region, more preferably 0.3 to 0.6, and most preferably substantially 0.5. Preferably the extent of the first region of conjunction which overlies the second region of conjunction is a proportion of the width of the first region taken along the side of the enclosure member, the second mentioned proportion having the same numerical value as the first mentioned proportion. Preferably the two sleeves are of the same shape and size.

The invention has particular application where the enclosure member is formed at least predominantly of flexible material and is capable of being inflated in use. In such an arrangement the sleeves may be so shaped that when inflated ready for use, with the sleeves protruding outwardly from the main body of the enclosure member prior to use, the general longitudinal axes of the sleeves are inclined to each other at a skew angle. In such a case when the enclosure member is inflated the regions of conjunction of the sleeves may have their greatest widths along directions inclined to each other and inclined to the horizontal in opposite senses.

Preferably the sleeves are so shaped that in use each region of conjunction has a width along the side of the enclosure member greater than its depth taken at right angles to the said width. Preferably the ratio of the length of each sleeve to the width thereof taken along the side of the enclosure member is in the range of 0.5:1 to 1.5:1, more preferably in the range 0.75:1 to 1.25:1, and most preferably the ratio is about 1:1. The sleeves may be shaped so as to fulfil the requirements of the above ratios when the enclosure member is arranged for normal use, or, where appropriate, when the enclosure member is laid flat for storage purposes, or may be so shaped as to fulfil the said requirements both when in use and when laid flat.

Preferably each sleeve is formed by two principal sleeve panels adapted to lie flat against each other substantially in register when the enclosure member is in a flattened state before use.

In some preferred arrangements, each sleeve consists of two sleeve panels joined together along join lines by joins in the materials thereof, the sleeve being adapted when laid flat before use to lie with the two sleeve panels flat against each other in register with the edges of the flattened panels defined by the said join lines.

Preferably each sleeve panel has the general shape of a triangle or of a truncated triangle with the apex of the triangle positioned opposite the region of conjunction of the sleeve with the main body of the enclosure member. Preferably the end of the sleeve remote from the said region of conjunction is provided with, or is adapted to be coupled to, a glove for use by an operator.

In a preferred arrangement according to the invention, the enclosure member is formed, at least in part, of sheets of flexible materials and includes an upper wall sheet, a lower wall sheet and a side sheet, the first sleeve being formed by an upper sleeve panel consisting of part of the upper wall sheet and a lower sleeve panel consisting of part of the side sheet, and the second sleeve being formed by an upper sleeve panel consisting of part of the side sheet and a lower sleeve panel consisting of part of the lower wall sheet.

Preferably the enclosure member has more than one pair of sleeves extending from the side of the main body of the enclosure member, and preferably the various regions of conjunction of the sleeves are arranged to overlap each other along the side of the enclosure member.

Conveniently each sleeve panel has the general shape of a triangle or a truncated triangle as set out hereinbefore, and the said side sheet conveniently has a shape defined substantially solely by two or more (where there are more than two sleeves) triangles or truncated triangles positioned with the bases of the alternate triangles abutting along a common line, the alternate triangles being offset from each other along the line. Preferably the alternate triangles are offset by half the length of the base of one of the triangles.

In accordance with another aspect of the present invention, there is provided an enclosure member for providing an environment isolated from the ambient environment, the enclosure member having first and second flexible sleeves extending from a side of a main body of the enclosure member, the general longitudinal axes of the sleeves being spaced apart along the side of the enclosure member, the enclosure member being formed at least in part of sheets of flexible material, and including an upper wall sheet, a lower wall sheet and a side sheet, wherein the first sleeve is formed by an upper sleeve panel consisting of part of the upper wall sheet and a lower sleeve panel consisting of part of the side sheet, and the second sleeve is formed by an upper sleeve panel consisting of part of the side sheet and a lower sleeve panel consisting of part of the lower wall sheet.

In accordance with another aspect of the present invention there is provided an enclosure member for providing an environment isolated from the ambient environment, the enclosure member having a sleeve extending from a region of conjunction of the sleeve with a main body of the enclosure member, the sleeve being so shaped that when the enclosure member is in normal use, the said region of conjunction is elongated to an extent greater than any elongation produced by normal positioning of the flexible material of the enclosure member.

Preferably the enclosure member has first and second flexible sleeves extending from a side of the main body of the enclosure member, the first sleeve extending from a first region of conjunction with the main body of the enclosure member, and the second sleeve extending from a second region of conjunction with the main body of the enclosure member, the general longitudinal axes of the sleeves being spaced apart along the side of the enclosure member for the sleeves to accommodate the arms of an operator manipulating objects within the enclosure member during normal use of the enclosure member, the sleeves being so shaped that when the enclosure member is in normal use, each said region of conjunction has a width along the side of the enclosure member greater than its depth in a vertical direction.

Preferably the ratio of the length of the or each sleeve to the width thereof is in the range 0.5:1 to 1.5:1, more preferably in the range 0.75:1 to 1.25:1, and most preferably the ratio is about 1:1.

There is further provided in accordance with the present invention a method of making an enclosure member for providing an environment isolated from the ambient environment, the method including the steps of joining together upper and lower sheets of flexible material and a side sheet of flexible material to form an enclosure member having first and second flexible sleeves extending from a side of a main body of the enclosure member, wherein the method includes forming the first sleeve by joining together an upper sleeve panel consisting of part of the upper wall sheet and a lower sleeve panel consisting of part of the side sheet, and forming the second sleeve by joining together an upper sleeve panel consisting of part of the side sheet and a lower sleeve panel consisting of part of the lower wall sheet.

There is yet further provided in accordance with the present invention a method of making an enclosure member for providing an environment isolated from the ambient environment, the method including the steps of joining together upper and lower sheets of flexible material and a side sheet of flexible material to form an enclosure member having first and second flexible sleeves extending from a side of a main body of the enclosure member, wherein the method includes the steps of forming the first sleeve by joining together an upper sleeve panel consisting of part of the upper wall sheet and a lower sleeve panel consisting of part of the side sheet to provide the first sleeve extending from a first region of conjunction with the main body of the enclosure member, and forming the second sleeve by joining together an upper sleeve panel consisting of part of the side sheet and a lower sleeve panel consisting of part of the lower wall sheet to provide the second sleeve extending from a second region of conjunction with the main body of the enclosure member, the enclosure member being produced by joining together substantially flat sheets of the said material in such a manner that the finished enclosure member is adapted to lie flat for storage purposes and when so lain the said first region of conjunction partially overlies the said second region of conjunction.

In accordance with another aspect of the present invention, there is provided a method of making an enclosure member for providing an environment isolated from the ambient environment, the method comprising the steps of joining together two or more sheets of flexible material to form an enclosure member having first and second flexible sleeves extending from the side of a main body of the enclosure member, the first sleeve extending from a firt region of conjunction with the main body of the enclosure member, and the second sleeve extending from a second region of conjunction with the main body of the enclosure member, the general longitudinal axes of the sleeves being spaced apart along the side of the enclosure member, wherein the method includes the steps of joining together the said two or more sheets along join lines substantially all of which are substantially straight lines, and wherein the arrangement of the join lines is such that the enclosure member is adapted to lie substantially flat for storage purposes with the said first region of conjunction of the first sleeve partially overlying the said second region of conjunction of the second sleeve.

It is to be appreciated that the various preferred features which have been set out in connection with the first apparatus aspect of the invention are also preferred as features, where appropriate, in connection with the other apparatus aspects of the invention. Furthermore the preferred features which have been set out in connection with the various apparatus aspects of the present invention are also preferred as features, where appropriate, in connection with the method aspects of the invention.

In all aspects of the present invention, it is preferred that the enclosure member is made of flexible, transparent, synthetic plastics material. Preferably the various joins referred to are made by heat sealing.

It is to be appreciated that where the side of the isolator is referred to without further definition, the side may be positioned horizontally, vertically, or inclined to these directions. Where terms such as upper and lower are used, it is to be appreciated that these refer to those embodiments which are adapted to be positioned in a particular configuration relative to the horizontal in normal use, and the terms upper and lower refer to the appropriate portions of the enclosure member when in position in normal use. Furthermore it is to be appreciated that in some embodiments, where appropriate, the said upper and lower sheets forming an enclosure member may be sheets formed from a continuous length of sheeting folded over upon itself. Similarly the side sheet may in some embodiments be formed integrally with the upper and/or lower sheets when the entire walling of the isolator is laid out flat as a blank prior to folding into the configuration ready for joining as set out above. That is to say that although when presented for joining, various parts of the enclosure member may be formed of a number of sheets to be joined together, these sheets may, in some arrangements, form various portions of a single sheeting blank.

Embodiments of the invention will now be described by way of example with reference to the accompanying drawings in which.

It is to be appreciated that the Figures referred to above are diagrammatic representations of embodiments of the present invention, and that in some cases details of elements allowing junction of the various components have been omitted for simplicity.

Figure 1:
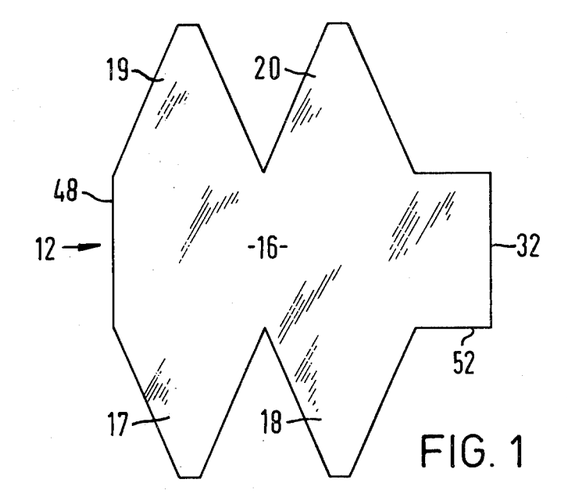
FIG. 1 is a front view of an upper wall sheet of an enclosure member embodying the invention.
Figure 2:
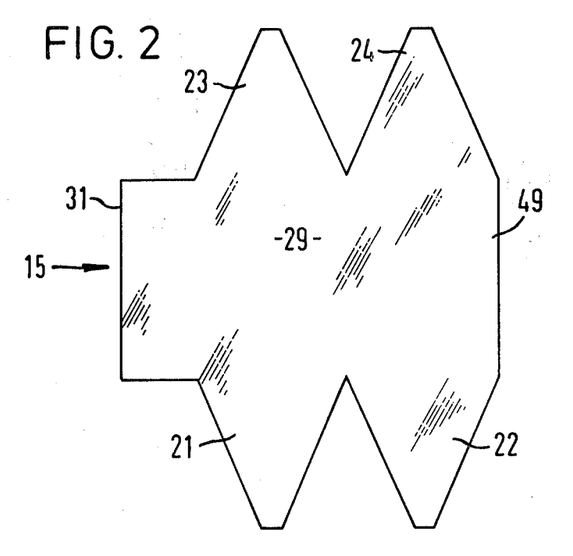
FIG. 2 is a plan view of a lower wall sheet of an enclosure member embodying the invention.
Figure 3:
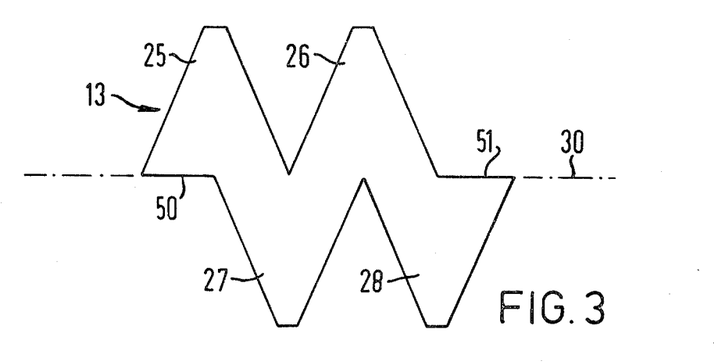
FIG. 3 is a plan view of a side sheet of the embodiment of the present invention, the side sheet being laid out in flattened form.
Figure 4:
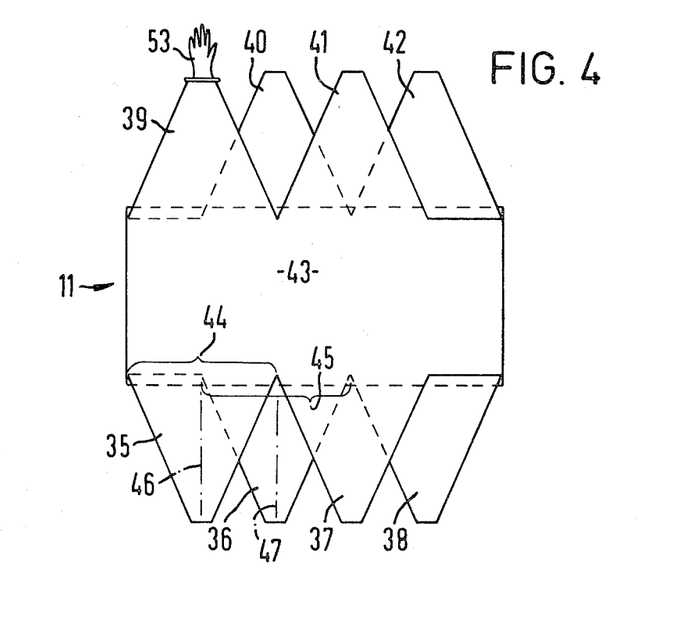
FIG. 4 is a plan view of the enclosure member embodying the present invention when laid out in flattened form.
Figure 5:
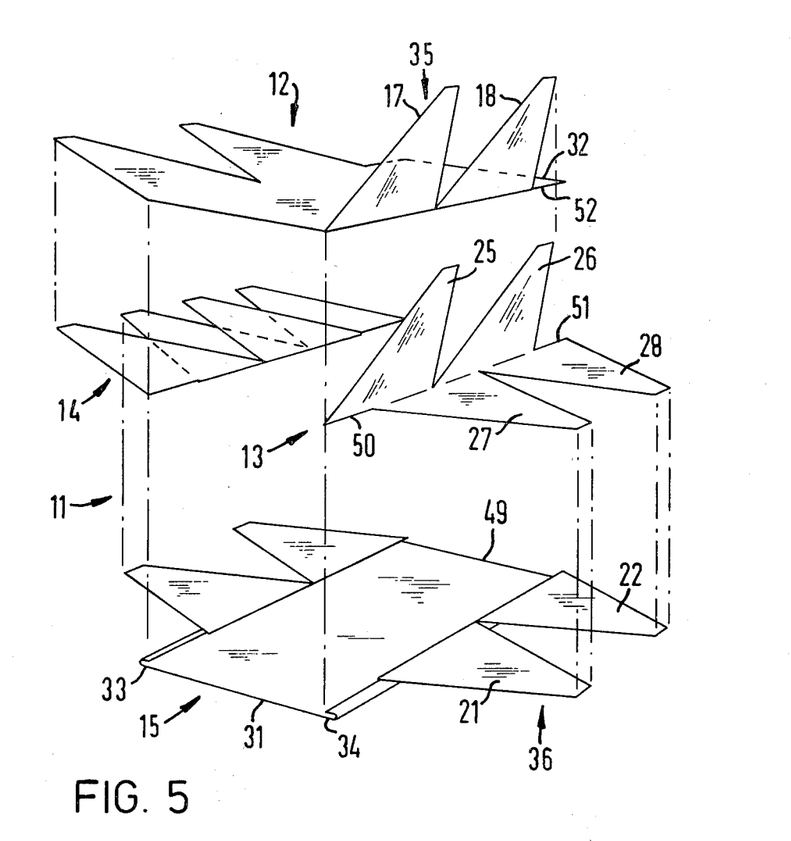
FIG. 5 is an exploded view of the main components of the enclosure member shown in FIG. 4.
Figure 6:
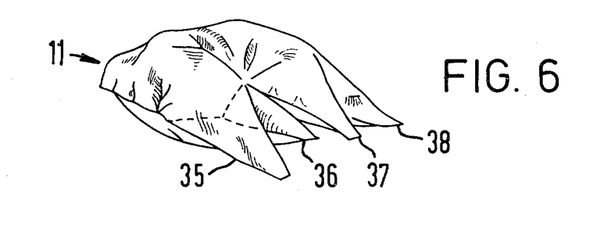
FIG. 6 is a perspective view of the enclosure member of FIG. 4 when inflated ready for use.

Referring firstly to FIGS. 1 to 6, and in particular initially to FIGS. 5 and 6, an enclosure member 11 adapted for use as an isolator for providing an environment isolated from the ambient environment is formed by an upper wall sheet 12 two side sheets 13 and 14 and a lower wall sheet 15, the sheet being made conveniently of flexible transparent synthetic plastics material such a polyethylene or polyvinyl chloride. As is shown in FIG. 1, the upper wall sheet 12 comprises a central portion 16 and outwardly protruding sleeve panels 17, 18, 19 and 20. Referring to FIG. 2, the lower wall sheet 15 correspondingly comprises a central portion 29 and sleeve panels 21, 22, 23 and 24. As is shown in FIG. 3, the side sheet 13 comprises four sleeve panels 25, 26, 27 and 28. Each sleeve panel has the shape of a truncated triangle positioned with the base of the triangle, the bases of the triangles being positioned along a substantially straight common line indicated at 30. Referring again to FIGS. 1 and 2, the width of the central portion 29 of the lower wall sheet 15 across an end of the sheet indicated at 31 is arranged to be slightly greater than the width of the central portion 16 of the upper wall sheet 12 across an end indicated at 32. The reason for this slightly greater width is to allow material to provide folded over portions 33 and 34 indicated in FIG. 5 on the lower wall sheet 15. The folded over portions 33 and 34 provide a more stable base for the enclosure member 11 when used as an exclusion isolator in the inflated exclusion mode.

When the sheets of FIGS. 1, 2 and 3 are jointed together, as will be described in more detail hereinafter, an enclosure member is provided having four pairs of sleeves extending outwardly from a main body of the enclosure member. In FIG. 4 the pairs of sleeves are indicated as sleeves 35 and 36, 37 and 38, 39 and 40, and 41 and 42. The main body of the enclosure member 11 is indicated at 43, and is formed predominantly by the central portion 16 of the upper sheet 12 shown in FIG. 1 and the central portion 21 of the lower wall sheet 15 is shown in FIG. 2. The detailed construction of the sleeves is best described by reference to one pair only of sleeves which wil be taken to be a first sleeve 35 and a second sleeve 36 extending from a side of the main body 43 of the enclosure member 11. As is shown in FIG. 4 and FIG. 6, the first sleeve 35 extends from a first region 44 of conjunction with the main body 43 of the enclosure member 11, and the second sleeve 36 extends from a second region 45 of conjunction with the main body 43. The sleeves 35 and 36 have general longitudinal axes indicated in FIG. 4 at 46 and 47 respectively, and the sleeves 35 and 36 are positioned with the axes 46 and 47 spaced apart along the side of the enclosure member 11 for the sleeves to accommodate the arms of an operator manipulating objects inside the enclosure member 11 during normal use of the enclosure member. As can be seen in FIGS. 4 and 6, the first region 44 of conjunction of the first sleeve 35 with the main body 43 partially overlies the second region 45 of conjunction of the second sleeve 36 with the main body 43 when viewed vertically from above when the enclosure member is in normal use.

Referring now particularly to FIG. 5, there will be explained the method of making the enclosure member 11 shown in the drawings. The main body 43 of the enclosure member is formed by joining the upper wall sheet 12 to the lower wall sheet 15 along straight lines and joins between the edge 31 and an edge 48 of the upper wall sheet 12, and between the edge 32 and an edge 49 of the lower wall sheet 15. These joins, and other joins between the sheets are conveniently effected by heat sealing. The first sleeve 35 is formed by joining the upper sleeve panel 17 of the upper wall sheet 12 to the lower sleeve panel 25 of the side sheet 13, and the second sleeve 36 is formed by joining the upper sleeve panel 27 of of the side sheet 13 to the lower sleeve panel 21 of the lower wall sheet 15.

As can be seen in FIG. 3, the triangular sleeve panels 25 and 26 are offset by half a pitch from the triangular sleeve panels 27 and 28 leaving edge portions 50 and 51 along the line 30. Referring again to FIG. 5, the edge portion 50 is joined to the folded over portion 34 of the lower wall sheet 15, and the edge portion 51 is joined to the upper wall sheet 12 at a side portion 52 adjacent the end edge 32. No join is made at the bases of the wall panels 17, 18, 21, 22, 27 and 26, and no join is made at the bases of the wall panels 25 and 28 except the joins already mentioned along the edge portions 50 and 51.

Similar junctions are made between the wall panels 19, 20, 23 and 24, and the side sheet 14, onthe far side of the enclosure member 11 as seen in FIG. 5. It is to be appreciated that the sheets shown in the Figures are shown in diagrammatic form, and in practice various minor extension pieces or flaps may be provided as appropriate, these elements having been omitted from the Figures for simplicity.

As shown in FIG. 4, the truncated end portions of the sleeves are adapted to be used for coupling to the sleeves gloves such as are indicated in one case at 53. The gloves may be attached, for example, as set out in the previous U.K. Pat. No. 1436104.

The embodiment of the present invention which has been described so far, gives rise to a number of advantages which derive either separately or in combination from various aspects of the present invention. A first advantage arises in that each sleeve allows greater freedom of movement for the operator's arm because of the relatively wide region of conjunction of the sleeve with the main body of the enclosure member compared with the normal region of conjunction which arises where a relatively narrow conical sleeve is joined to an enclosure member around a circular opening. Although the wide region of conjunction in accordance with the present invention gives freedom of movement in all directions, the sleeve shape is arranged to provide an elongated slot-like opening at the region of conjunction which particularly facilitates the horizontal movements which are largely required by the arms of the operator. In fact, as shown in FIG. 6, in the particular embodiment shown the widest part of the region of conjunction occurs across a line inclined to the horizontal, but this inclination is relatively small. The relatively wide region of conjunction in accordance with the present invention also brings the advantage that a sleeve can be produced from two laid flat sleeve panels joined along straight join lines, without the usual disadvantage of puckering and wrinkling when the flat joined sleeve is 'rounded out' by insertion of the operator's arm.

Another advantage which arises from the embodiment described comes from the arrangement that the first region of conjunction 44 partially overlies the second region of conjunction 45 when viewed vertically from above as shown particularly in FIGS. 4 and 6. This overlying effect of the adjacent pair of sleeves allows the general longitudinal axes of the sleeves to be placed relatively close together, at the distance required by the shoulder width of the operator, whilst allowing sufficient material in the sleeves to provide for 'rounding out' of the flat joined sleeve, and also whilst allowing the freedom of movement provided by the relatively wide regions of conjunction of the sleeves. If the adjacent sleeves 35 and 36 were to be positioned side by side in accordance with known practice, either the width of the regions of conjunction would need to be reduced, with consequent reduction of freedom of movement, or alternatively the sleeves would need to be space so wide apart that the general longitudinal axes would not be in the position required to accommodate the arms of the operator.

A third advantage which arises is that an easier and cheaper manufacturing technique can be used for making the isolator. The shapes of the upper and lower wall sheets and the two side sheets can be welded from flat sheets in a series of simple operations, and the welds required can be produced more easily than the circular welds which are required with previously known arrangements. It is then possible to use any thermo-weldable flexible plastics material rather than being limited to those particular materials (such as P.V.C.) which can be welded by radio frequency welding. Thus embodiments of the invention can be constructed by simpler processes in which the heating is generated in the die and then conducted to the plastics material, rather than being limited to radio frequency heating in which the heat is generated in the plastics itself. The latter method is required where more complicated circular welds are used. By way of example, polyethylene may be used in thermo-welding.

Figure 7:
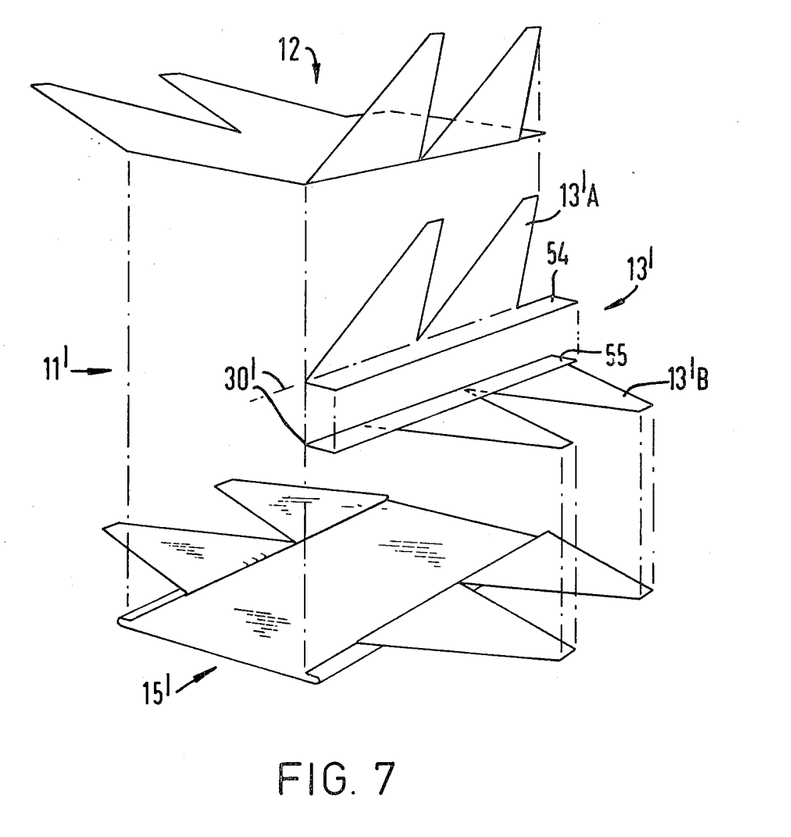
FIG. 7 is an exploded view of a modified enclosure member embodying the present invention.

There will now be described with reference to FIG. 7 a modification of the embodiment shown in the preceding Figures. In the embodiment of FIG. 7, the main elements perform the same function as in the previous embodiment, and components corresponding to those in the preceding Figures are indicated by like reference numerals except that the components in FIG. 7 are indicated with primed reference numerals. The modification of the embodiment of FIG. 7 consists in that the side sheet 13' is composed of two subsidiary side sheets 13'A and 13'B which are provided with two longitudinal flaps 54 and 55 respectively along the base line 30' common to the wall panels of the sheets 13'A and 13'B.

The modification of FIG. 7 provides a convenient method of construction in that the upper side sheet 13'A can first be joined to the upper wall sheet 12' and the lower side sheet 13'B can be joined to the lower wall sheet 15, and then the two subsidiary side sheets 13'A and 13'B can be joined together along the flaps 54 and 55.

Figure 8:
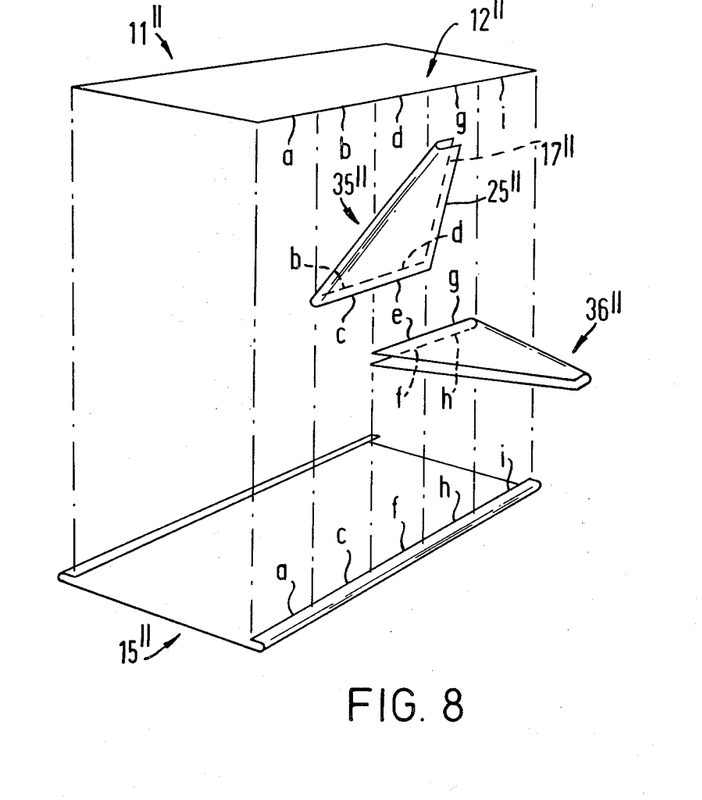
FIG. 8 is an exploded view of a further modified enclosure member embodying the present invention.

In FIG. 8 there is shown a further modification of the basic enclosure member shown in FIGS. 1 to 6, and in FIG. 8 components corresponding to components shown in previous Figures are indicated by double-primed reference numerals. For simplicity only two sleeves are shown in FIG. 8 and these are indicated as sleeves 35" and 36". The sleeve 35" comprises two sleeve panels 17" and 25" but these are formed by a single sheet of flexible plastics material which is initially separate from upper and lower wall sheets 12" and 15", and which is folded over on itself to form the sleeve 35". The sleeve 36" is constructed in a similar manner. In FIG. 8, the region of conjunction of the sleeve 35" with the main body of the enclosure member 11" is defined by the inner edges of the sleeve 35" which are indicated at b, c, d and e. The same letters b, c, d and e are also used to indicate the regions of the upper sheet 12", the second sleeve 36" and the lower sheet 15", to which the corresponding parts of the sleeve 35" are attached when the enclosure member 11" is assembled. Further edge portions of the sleeve 36" are indicated at f, g and h, and these letters are also used to indicate the corresponding regions of the upper sheet 12", and lower sheet 15" to which the edge portions are attached. Finally, edge portions a and i are indicated on the upper and lower wall sheets 12" and 15" to indicate edge regions which are attached together upon assembly.

In other modifications (not shown) of the embodiments described, the upper and lower wall sheets 12 and 15 may be formed as a single sheet folded over at the edge region indicated at 32 and 49 at FIG. 5. Alternatively, if required, the side sheet 13 in FIG. 5 may be formed from a continuous sheet with the upper wall sheet 12, for example being continuous at, and folded about, the outer truncated ends of the sleeve panels 17, 18, 25 and 26 respectively. Such an arrangement can be continued further, so that, for example, the entire group of four sheets shown in FIG. 5 may be formed from a continuous single sheet by having fold lines at three out of four of the four sets of truncated apexes of the triangular wall panels. Thus in such an arrangement when unfolded, in the shape of a blank, the single sheet could be enumerated say from left to right as comprising the upper sheet 12, the side sheet 13, the lower sheet 15, and the side sheet 14. It will be appreciated that many other arrangements of the sheets can be arrived at in order to fit the sheet into a single continuous blank, without departing from the scope of the present invention.

I claim:

1. An elongated enclosure member for providing an environment isolated from the ambient environment and adapted to be used in an exclusion mode to have a super-atmospheric pressure therein, or in a containment mode to have a sub-atmospheric pressure therein, the enclosure member including a main body defining a chamber extending along a longitudinal axis and having first and second flexible sleeves extending laterally with respect to a side of the main body of the enclosure member and substantially adjacent to each other, the first sleeve having a first end the periphery of which defines a first arm access opening in conjunction with the main body of the enclosure member, and the second sleeve having a first end the periphery of which defines a second arm access opening in conjunction with the main body of the enclosure member, said first and second sleeves each having an opposed second end the periphery of which is provided with or adapted to be secured to a plastic glove, each sleeve, when in its extended state with respect to said main body, extending within a plane individual to said sleeve which is normal to the longitudinal axis of said main body and which intersects the center of said arm access opening of said sleeve, wherein said planes extending through said arm access opening centers are spaced apart to define a space designated as the chest space to accommodate the body of an operator when the arms of the operator are raised to be horizontal in said sleeves, said first and second arm access openings being positioned with respect to said side of said main body and sized to accommodate the arms of an operator manipulating objects inside the enclosure member during normal use of the enclosure member such that, when said sleeves are inside and extend horizontally with respect to said main body, said sleeves are spaced apart with respect to said longitudinal axis of said main body and said first and second arm access openings are in abutting side-by-side relation and a line intersecting the center of each arm access opening lies at an acute angle with respect to the longitudinal axis of said chamber, whereby both sleeves are intersected by a plane mid-way between the sleeves extending normal to the longitudinal axis of said main body.

2. An enclosure member according to claim 1 wherein said first and second arm access openings are positioned on said main body such that the distance between two planes extending tangentially from respective peripheral edges of the arm access openings and extending normally to the longitudinal axis of the said main body lie in the range 0.25 to 0.75 of the width of one of the said arm access openings.

3. An enclosure member according to claim 2 in which the said distance lies in the range 0.3 to 0.6 of the width of one of said arm access openings.

4. An enclosure member according to claim 3 in which the said distance is substantially 0.5 of the width of one of said arm access openings.

5. An enclosure member according to claim 1 in which the two sleeves are of the same shape and size.

6. An enclosure member according to claim 1, in which the enclosure member is formed at least predominantly of flexible material and is inflated prior to use in an exclusion mode, the sleeves being so shaped that when inflated and ready for use, the sleeves protrude outwardly with respect to a side of the main body of the enclosure member and the general longitudinal axes of the sleeves are inclined to each other at a skew angle.

7. An enclosure member according to claim 6 in which the arm access openings of the sleeves have their greatest widths along directions inclined to each other and inclined to the horizontal in opposite senses.

8. An enclosure member according to claim 1 in which the sleeves are so shaped that in use each arm access opening has a width in the direction of the longitudinal axis of the enclosure member greater than its depth taken at right angles to the said width.

9. An enclosure member according to claim 1, in which the ratio of the length of each sleeve to the width of the arm access opening in the direction of the longitudinal axis of the enclosure member is in the range 0.5:1 to 1.5:1.

10. An enclosure member according to claim 9 in which the said ratio is in the range 0.75:1 to 1.25:1.

11. An enclosure member according to claim 10 in which the said ratio is about 1:1.

12. An enclosure member according to claim 1, in which each sleeve has the general shape of a truncated triangle with the apex of the triangle positioned opposite the conjunction of the sleeve with the main body of the enclosure member.

13. An enclosure member according to claim 1 in which the enclosure member when laid flat in a plane in a non-erected state is formed at least in part of sheets of flexible material and includes an upper wall sheet, a lower wall sheet and a side sheet, the first sleeve being formed by an upper sleeve panel consisting of part of the upper wall sheet and a lower sleeve panel consisting of part of the side sheet, and the second sleeve being formed by an upper sleeve panel consisting of part of the side sheet and a lower sleeve panel consisting of part of the lower wall sheet.

14. An enclosure member according to claim 1, in which the enclosure member has more than one pair of sleeves extending laterally with respect to the body of the enclosure member, and the various conjunctions of the sleeves are arranged to overlap each other along the side of the enclosure member.

15. An enclosure member according to claim 14 in which each sleeve panel has the general shape of a truncated triangle with the apex of the triangle positioned opposite the conjunction of the sleeve with the main body of the enclosure member, and in which the said side sheet has a shape defined substantially solely by the said truncated triangles positioned with the bases of alternate triangles abutting along a common line, the alternate triangles being offset from each other along the line.

16. An enclosure member according to claim 15 in which the alternate triangles are offset by half the length of the base of one of the triangles.

17. An enclosure member according to claim 1 in which the enclosure member is formed at least predominantly of flexible material, the sleeves being so shaped that when erected ready for use, the sleeves protrude inwardly with respect to a side of the main body of the enclosure member and the general longitudinal axes of the sleeves are inclined to each other at a skew angle.

* * * * *